US006595036B1

(12) United States Patent
Nakai

(10) Patent No.: US 6,595,036 B1
(45) Date of Patent: Jul. 22, 2003

(54) METHOD AND APPARATUS FOR MEASURING AMOUNT OF GAS ADSORPTION

(75) Inventor: Kazuyuki Nakai, Osaka (JP)

(73) Assignee: Bel Japan, Inc., Osaka (JP)

( * ) Notice: Subject to any disclaimer, the term of this patent is extended or adjusted under 35 U.S.C. 154(b) by 0 days.

(21) Appl. No.: 10/083,609

(22) Filed: Feb. 27, 2002

(51) Int. Cl.[7] .......................... G01N 15/08; G01M 3/02; G01M 3/36
(52) U.S. Cl. ..................... 73/19.05; 73/23.21; 73/31.05; 422/69; 422/88
(58) Field of Search .............................. 73/19.05, 19.01, 73/23.2, 31.05, 23.35, 23.21, 1.03, 866; 422/69, 88

(56) References Cited

U.S. PATENT DOCUMENTS

| 3,222,133 A | * | 12/1965 | Ballou et al. .................. 23/230 |
| 3,262,319 A | * | 7/1966 | Orr, Jr. et al. ................. 73/432 |
| 3,349,625 A | * | 10/1967 | Benusa et al. ................. 73/432 |
| 3,464,273 A | * | 9/1969 | Hendrix et al. ................ 73/432 |
| 3,500,675 A | * | 3/1970 | Sandstede et al. .......... 73/19.01 |
| 3,555,912 A | * | 1/1971 | Lowell ......................... 73/432 |
| 3,707,870 A | * | 1/1973 | Herve et al. ..................... 73/38 |
| 3,732,736 A | * | 5/1973 | Glaude et al. ........... 73/432 PS |
| 3,850,040 A | | 11/1974 | Orr, Jr. et al. ............ 73/432 PS |
| 4,693,124 A | | 9/1987 | Killip et al. .............. 73/863.11 |
| 4,944,273 A | * | 7/1990 | Baresel et al. ............... 123/440 |
| 5,239,859 A | * | 8/1993 | Lehmann .................... 73/49.2 |
| 5,355,739 A | * | 10/1994 | Cooper et al. ........... 73/864.73 |
| 5,578,505 A | * | 11/1996 | Nuttall et al. .................. 437/8 |
| 5,600,996 A | * | 2/1997 | Witschi ....................... 73/49.2 |
| 5,629,474 A | * | 5/1997 | Williams .................... 73/23.2 |
| 5,780,716 A | * | 7/1998 | Shimizu et al. ............. 73/23.2 |
| 5,899,702 A | * | 5/1999 | Nuttall et al. ................. 438/14 |
| 6,305,215 B2 | * | 10/2001 | Lehmann .................... 73/49.3 |
| 6,474,138 B1 | * | 11/2002 | Chang et al. .............. 73/25.01 |

FOREIGN PATENT DOCUMENTS

| JP | 61-79130 | 4/1986 |
| JP | 63-295943 | 12/1988 |

* cited by examiner

*Primary Examiner*—Helen Kwok
*Assistant Examiner*—David J. Wiggins
(74) *Attorney, Agent, or Firm*—Armstrong, Westerman & Hattori, LLP

(57) ABSTRACT

In a volumetric gas adsorption measuring method, an initial dead volume of the sample cell and an initial dead volume of a reference cell at the same time point are preliminarily determined. When the gas adsorption on the solid sample is to be measured, a change in the dead volume of the sample cell is calculated on the basis of an internal gas with the sample cell and reference cell immersed in a pressure of the reference cell measured at this time point cryogenic fluid temperature bath, the initial dead volume of the reference cell, and an initial gas pressure of the reference cell measured at a time point of the measurement of the initial dead volume of the reference cell. Then, the initial dead volume of the sample cell preliminarily measured is corrected on the basis of the change in the dead volume of the sample cell for the calculation of the amount of the gas adsorbed on the solid sample.

17 Claims, 4 Drawing Sheets

METHOD AND APPARATUS FOR MEASURING AMOUNT OF GAS ADSORPTION

BACKGROUND OF THE INVENTION

1. Field of the Invention

The present invention relates to a method and an apparatus for measuring the amount of a gas adsorbed on a solid material.

2. Description of Related Art

For advantageous use of solid materials such as powdery materials, adsorbents and films, it is important to obtain information on the specific surface area and pore size distribution of such a solid material. To obtain such information, it is necessary to prepare an adsorption isotherm by measuring gas adsorption on the solid material while maintaining the solid material at a constant temperature.

For example, a volumetric gas adsorption measuring apparatus as shown in FIG. 4 is employed for the measurement of the gas adsorption on the solid material. As shown, the volumetric gas adsorption measuring apparatus 50 includes: a manifold 51 maintained at a predetermined temperature (T) and having a known geometric volume (Vs); a sample cell 52 which contains a solid sample A and is connected to the manifold 51 via a valve 54; and a constant temperature bath 53 which contains a cryogenic coolant such as liquid nitrogen. A gas inlet/outlet line is connected to the manifold 51 via a valve 55, and a sample retaining portion 52a of the sample cell 52 is immersed in the cryogenic coolant contained in the constant temperature bath 53 for maintaining the solid sample A at a cryogenic temperature.

With the use of the volumetric gas adsorption measuring apparatus 50, the amount of a gas adsorbed on the solid sample A is measured in the following manner. First, the manifold 51 and the sample cell 52 are evacuated with the valves 54 and 55 being open. Then, the gas is fed into the manifold 51 with the valve 54 being closed, and the valve 55 is closed. At this time point, a gas pressure (Pi) is measured. Subsequently, the valve 54 is opened, and the gas is introduced from the manifold 51 into the sample cell 52 thereby to be adsorbed on the solid sample A within the sample cell 52. When an adsorption equilibrium is reached, a gas pressure (Pe) is measured.

Provided that the gas fed into the manifold 51 is an ideal gas, the following expression is satisfied:

$$PiVs = n_1 RT$$

$$Pe(Vs+Vd) = n_2 RT$$

wherein Vd is a dead volume of the sample cell 52 (i.e., the volume of the sample cell 52 excluding the volume of the solid sample A on the assumption that the gas introduced into the sample cell 52 is maintained at the same temperature as in the manifold 51), $n_1$ is the number of moles of the gas fed into the manifold 51, $n_2$ is the number of moles of the gas after the adsorption, and R is the gas constant. Therefore, the amount (N) of the gas adsorbed on the solid sample A is expressed by:

$$N = n_1 - n_2 = [(Pi-Pe)Vs - PeVd]/RT$$

Therefore, the dead volume (Vd) of the sample cell 52 is generally determined prior to the measurement of the gas adsorption on the solid sample A. More specifically, the manifold 51 and the sample cell 52 are evacuated with the valves 54 and 55 being open. Thereafter, a non-adsorbable gas which is not adsorbed on the solid sample A is fed into the manifold 51 with the valve 54 being closed, and then the valve 55 is closed. At this time point, a gas pressure (P1) is measured. Subsequently, the valve 54 is opened to introduce the non-adsorbable gas from the manifold 51 into the sample cell 52 retaining the solid sample A. At this time point, a gas pressure (P2) is measured.

Provided that the non-adsorbable gas fed into the manifold 51 is an ideal gas, the following expression is satisfied:

$$P1Vs = nRT$$

$$P2(Vs+Vd) = nRT$$

wherein n is the number of moles of the non-adsorbable gas fed into the manifold 51, and R is the gas constant. Therefore, the dead volume (Vd) of the sample cell 52 is expressed by:

$$Vd = (P1-P2)Vs/P2$$

Thus, the measurement of the gas adsorption on the solid sample A can be achieved by preliminarily determining the dead volume (Vd) of the sample cell 52 retaining the solid sample A. Since the aforesaid adsorption isotherm indicates a change in the gas adsorption (N) on the solid sample A observed when the ratio Pe/Ps of the gas pressure (Pe) in adsorption equilibrium to the saturation vapor pressure (Ps) of the adsorbable gas is changed from zero to one, the aforesaid process is repeatedly performed for the preparation of the adsorption isotherm. That is, the amounts (N) of the gas adsorbed on the solid sample A are determined while the gas pressure (Pe) in adsorption equilibrium is progressively changed. Therefore, the measurement of the adsorbed gas amounts (N) for the preparation of the adsorption isotherm is a time-consuming operation.

Further, the cryogenic coolant such as liquid nitrogen contained in the constant temperature bath 53 is highly evaporative, so that the surface level of the cryogenic coolant is remarkably lowered with time. Even if the sample retaining portion 52a is completely submerged in the cryogenic coolant, the environment (temperature) of the sample cell 52 above the surface level of the cryogenic coolant constantly changes as the surface level of the cryogenic coolant is lowered. As a result, the dead volume (Vd) of the sample cell 52 is changed.

For accurate determination of the gas adsorption on the solid sample A, the dead volume (Vd) of the sample cell 52 should be determined every time the adsorbed gas amount (N) is to be measured. Thus, the preparation of the adsorption isotherm is a troublesome operation.

Therefore, consideration is given to the conventional volumetric gas adsorption measuring apparatus 50 for constantly maintaining the surface level of the cryogenic coolant with respect to the sample cell 52 immersed in the cryogenic coolant, so that the dead volume (Vd) of the sample cell 52 initially determined can be employed for the measurement of the gas adsorption to be performed later. This eliminates the need for determining the dead volume (Vd) of the sample cell 52 every time the amount (N) of the gas adsorbed on the solid sample A is measured.

A common approach is to provide a lift mechanism for moving up and down the constant temperature bath 53 so that the surface level of the cryogenic coolant is constantly kept at a predetermined height with respect to the sample cell 52, or to provide a coolant supplying mechanism for replenishing the constant temperature bath 53 with the cryogenic coolant so as to prevent the change in the surface level of the cryogenic coolant within the constant temperature bath 53. In either case, the change in the surface level of the cryogenic coolant should be detected by means of a temperature sensor or the like for actuation of the lift mechanism or the coolant supplying mechanism. Therefore, an expensive temperature sensor should be employed for accurate detection of an abrupt temperature change, thereby increasing the costs. Further, the accuracy of the temperature sensor may be reduced by corrosion or frosting of a temperature sensing probe of the sensor.

Another conceivable approach is to provide a cryogenic coolant outlet at a predetermined height of the constant temperature bath 53 so that the surface level of the cryogenic coolant within the constant temperature bath 53 is kept constant by continuously supplying the cryogenic coolant to the constant temperature bath 53 and constantly letting out the cryogenic coolant from the outlet of the constant temperature bath 53. This approach requires a cryogenic coolant circulating mechanism, thereby complicating the construction of the overall apparatus.

Rather than maintaining the surface level of the cryogenic coolant at the constant level, further another conceivable approach is to cover the sample cell 52 to a predetermined height with a cylindrical jacket of a porous material (e.g., ceramic) which can suck up the cryogenic coolant from a lower portion thereof immersed in the cryogenic coolant by capillary action or to cover the sample cell 52 to a predetermined height with a cylindrical jacket of a highly heat-conductive metal material having a lower portion immersed in the cryogenic coolant, whereby the environment of the sample cell 52 is maintained in a generally constant state. However, this approach often fails to assuredly maintain the environment of the sample cell 52 in the constant state if the change in the surface level of the cryogenic coolant increases.

Further, the jacket of the porous material is cooled to a cryogenic temperature when sucking up the cryogenic coolant. Therefore, the jacket adsorbs moisture in air immediately after being detached from the sample cell upon completion of the measurement of the gas adsorption. It is cumbersome to dry the jacket before the jacket is reused.

It is therefore an object of the present invention to provide a method and an apparatus for measuring gas adsorption, which ensure easy and accurate measurement of the amount of a gas adsorbed on a solid material without the need for maintaining the environment of a sample cell in a constant state.

SUMMARY OF THE INVENTION

In accordance with the present invention to achieve the aforesaid object, there is provided a method for measuring an amount of a gas adsorbed on a solid sample, the method comprising: a preparatory process which comprises the steps of: preliminarily determining a dead volume of a reference cell for determination of a dead volume of a sample cell which retains the solid sample and, at this time point, filling and confining the gas in the reference cell; measuring an initial dead volume of the sample cell and an initial internal gas pressure of the reference cell with the sample cell and the reference cell being immersed in a cryogenic coolant contained in a constant temperature bath; and calculating an initial dead volume of the reference cell at a time point of the measurement of the initial dead volume of the sample cell on the basis of the initial internal gas pressure of the reference cell and the preliminarily measured dead volume of the reference cell; and a gas adsorption determining process which comprises the steps of: feeding the gas into a reference volume portion having a known geometric volume with the sample cell and the reference cell being immersed in the cryogenic coolant within the constant temperature bath, and measuring an internal gas pressure of the reference volume portion; allowing the reference volume portion to communicate with the sample cell to introduce the gas from the reference volume portion into the sample cell, and measuring an internal gas pressure of the sample cell; and calculating the amount of the gas adsorbed on the solid sample on the basis of the internal gas pressure of the reference volume portion, the internal gas pressure of the sample cell and the dead volume of the sample cell, wherein the dead volume of the sample cell to be employed for the calculation of the amount of the gas adsorbed on the solid sample is determined in the gas adsorption determining process by measuring an internal gas pressure of the reference cell at a time point of the measurement of the internal gas pressure of the sample cell, and correcting the initial dead pressure of the reference cell and the preliminarily measured dead volume of the reference cell. When the amount of the gas adsorbed on the solid sample is measured, the initial dead volume of the sample cell is corrected on the basis of the internal gas pressure of the reference cell measured at the time point of the measurement of the internal gas pressure of the sample cell, the initial dead volume of the reference cell and the initial internal gas pressure of the reference cell. Then, the corrected dead volume of the sample cell is employed for the calculation of the amount of the gas adsorbed on the solid sample. Therefore, the inventive method obviates the need for performing the troublesome operation for determining the dead volume of the sample cell every time the amount of the gas adsorbed on the solid sample is measured. In addition, there is no need to maintain the environment of the sample cell in a constant state as in the conventional volumetric gas adsorption measuring method. Hence, the amount of the gas adsorbed on the solid sample can easily and accurately be determined.

Where the reference cell has the same inner diameter as a portion of the sample cell which is subjected to a change in the surface level of the cryogenic coolant when being immersed in the cryogenic coolant within the constant temperature bath, a change volume of the sample cell on the basis of the internal gas pressure of the reference cell measured at the time point of the measurement of the internal gas pressure of the sample cell, the initial dead volume of the reference cell and the initial internal gas pressure of the reference cell.

The dead volume of the sample cell is herein defined as the apparent volume of the sample cell excluding the volume of the solid sample on the assumption that the sample cell is entirely maintained at the same temperature as the reference volume portion, and the dead volume of the reference cell is herein defined as the apparent volume of the reference cell on the assumption that the reference cell is entirely maintained at the same temperature as the reference volume portion.

In the gas adsorption measuring method, the dead volume of the reference cell is preliminarily measured and, at this time point, the gas is fed and confined in the reference cell. Then, the initial dead volume of the sample cell and the initial internal gas pressure of the reference cell are measured. The initial dead volume of the reference cell at the time point of the measurement of the initial dead volume of the sample cell is calculated on the basis of the initial internal gas in the dead volume of the reference cell accords with a change in the dead volume of the sample cell. Therefore, the initial dead volume of the sample cell can easily be corrected.

Alternatively, the preparatory process may comprise the steps of: providing, instead of the reference cell, a sensor having a physical property value which is variable proportionally to the change in the surface level of the cryogenic coolant within the constant temperature bath for determination of the dead volume of the sample cell; measuring the initial dead volume of the sample cell and an initial physical property value of the sensor with the sample cell and the sensor being immersed in the cryogenic coolant within the constant temperature bath; and calculating, as a conversion factor, a ratio of a change in the dead volume of the sample cell to the change in the physical property value of the sensor occurring due to the change in the surface level of the cryogenic coolant, wherein the dead volume of the sample cell to be employed for the calculation of the amount of the gas adsorbed on the solid sample is determined in the gas adsorption determining process by measuring a physical property value of the sensor at a time point of the measurement of the internal gas pressure of the sample cell, and correcting the initial dead volume of the sample cell on the basis of the physical property value of the sensor measured at the time point of the measurement of the internal gas pressure of the sample cell, the initial physical property value of the sensor, and the conversion factor. In this method, the amount of the gas adsorbed on the solid sample can easily and accurately be determined.

Alternatively, the preparatory process may comprise the steps of: immersing the sample cell in the cryogenic coolant within the constant temperature bath, and preliminarily determining, as a function of time, the change in the dead volume of the sample cell occurring with time due to lowering of the surface level of the cryogenic coolant within the constant temperature bath; and measuring the initial dead volume of the sample cell with the sample cell being immersed in the cryogenic coolant within the constant temperature bath, wherein the dead volume of the sample cell to be employed for the calculation of the amount of the gas adsorbed on the solid sample is determined in the gas adsorption determining process by determining an amount of the change in the dead volume of the sample cell at the time point of the measurement of the internal gas pressure of the sample cell on the basis of the function according to time elapsed from the time point of the measurement of the initial dead volume of the sample cell, and correcting the initial dead volume of the sample cell on the basis of the amount of the change in the dead volume of the sample cell at the time point of the measurement of the internal gas pressure of the sample cell.

In this method, the change in the dead volume occurring due to the lowering of the surface level of the cryogenic coolant within the constant temperature bath is preliminarily determined as the function of time as described above. When the amount of the gas adsorbed on the solid sample is measured, the initial dead volume of the sample cell previously measured is corrected by determining the amount of the change in the dead volume of the sample cell on the basis of the function according to the time elapsed from the time point of the measurement of the initial dead volume of the sample cell. Therefore, the amount of the gas adsorbed on the solid sample can more efficiently be determined without the need for actually measuring the amount of the change in the dead volume of the sample cell before the determination of the adsorbed gas amount.

The foregoing and other objects, features and effects of the present invention will become more apparent from the following description of the preferred embodiments with reference to the attached drawings.

DESCRIPTION OF PREFERRED EMBODIMENTS

Figure 1:
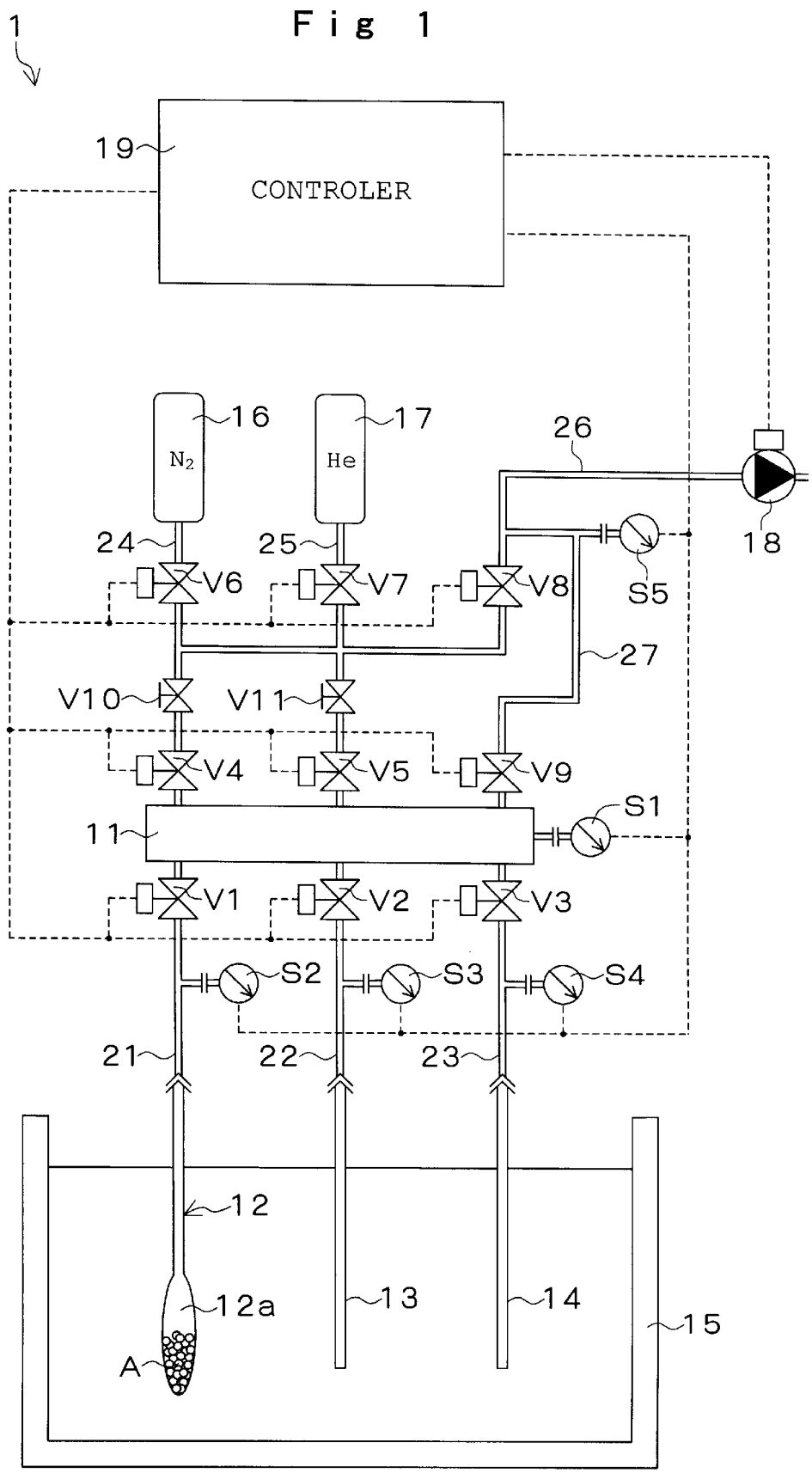
FIG. 1 is a diagram schematically illustrating the construction of a gas adsorption measuring apparatus according to one embodiment of the present invention.

Embodiments of the present invention will hereinafter be described with reference to the attached drawings. A gas adsorption measuring apparatus 1 as shown in FIG. 1 includes: a manifold 11 having a known geometric volume Vs; a sample cell 12 having a sample retaining portion 12a for retaining a solid sample A and connected to the manifold 11 via a cell connection pipe 21 having an electromagnetic valve V1; a first reference cell 13 connected to the manifold 11 via a cell connection pipe 22 having an electromagnetic valve V2 for determining a-change in the dead volume of the sample cell 12; a second reference cell 14 connected to the manifold 11 via a cell connection pipe 23 having an electromagnetic valve V3 for measuring the saturation vapor pressure of an adsorbable gas; a constant temperature bath 15 containing liquid nitrogen as a cryogenic coolant in which the sample retaining portion 12a of the sample cell 12, the first reference cell 13 and the second reference cell 14 are immersed; an adsorbable gas cylinder 16 connected to the manifold 11 via a gas inlet pipe 24 having electromagnetic valves V4, V6 and a needle valve V10 and charged with nitrogen gas as the adsorbable gas; and a non-adsorbable gas cylinder 17 connected to the manifold 11 via a gas inlet pipe 25 having electromagnetic valves V5, V7 and a needle valve V11 and charged with helium gas as a non-adsorbable gas. The electromagnetic valves V1 to V7 are opened and closed as required for feeding the adsorbable nitrogen gas or the non-adsorbable helium gas into the manifold 11, the sample cell 12, or the reference cells 13, 14.

The reference cells 13, 14 each have the same inner diameter as a portion of the sample cell 12 excluding the sample retaining portion 12a. With the sample cell 12 and the reference cells 13, 14 being immersed in the liquid nitrogen within the constant temperature bath 15, the surface level of the liquid nitrogen changes along the same diameter portions of the respective cells. The sample cell 12 and the reference cells 13, 14 are each composed of a glass, a ceramic, a metal, an organic material or the like. The sample cell 12 and the first reference cell 13 are preferably composed of the same material.

The gas inlet pipes 24, 25 communicate with each other at points thereof located between the electromagnetic valve V6 and the needle valve V10 and between the electromagnetic valve V7 and the needle valve V11. The needle valve V10 has a smaller throttle rate than the needle valve V11. Therefore, the nitrogen gas or the helium gas can be fed from the adsorbable gas cylinder 16 or from the non-adsorbable gas cylinder 17 into the manifold 11 through either of portions of the gas inlet pipes 24, 25 downstream of the communication points thereof by selectively opening and closing the electromagnetic valves V4 and V5, and a gas feed rate can be changed by feeding the gas selectively through the portions of the gas inlet pipes 24, 25 downstream of the communication points thereof.

A gas outlet pipe 26 provided with an electromagnetic valve V8 and a vacuum pump 18 is connected to the gas inlet pipes 24, 25, and further connected to the manifold 11 via a gas outlet pipe 27 having an electromagnetic valve V9. The gas inlet pipes 24, 25, the manifold 11, and the sample cell 12 and the reference cells 13, 14 connected to the manifold 11 can be evacuated by selectively opening and closing the electromagnetic valves V8 and V9.

The manifold 11 and the cell connection pipes 21, 22 and 23 are respectively provided with pressure sensors S1, S2, S3 and S4, and the gas outlet pipe 27 is provided with a vacuum sensor S5. The gas adsorption measuring apparatus 1 further includes a controller 19 which controls the opening and closing of the respective electromagnetic valves V1 to V9 and the evacuation by the vacuum pump 18 on the basis of gas pressures detected by the pressure sensors S1 to S4 and the vacuum sensor S5 and performs computing operations for calculation of the dead volumes of the sample cell 12 and the reference cells 13, 14 and an adsorbed gas amount.

Next, an explanation will be given to a process for determining the amount of the adsorbable gas (nitrogen gas) adsorbed on the solid sample A by means of the gas adsorption measuring apparatus 1.

Initialization of Apparatus

Before the sample cell 12 and the reference cells 13 and 14 are respectively connected to the cell connection pipes 21, 22 and 23 with the electromagnetic valves V1 to V9 being closed, the gas inlet pipes 24, 25 are evacuated with the electromagnetic valve V8 being open.

After the electromagnetic valves V1 to V3 are opened to open the cell connection pipes 21, 22, 23 to the atmosphere, the electromagnetic valve V9 is opened and the electromagnetic valves V1 to V3 are closed. Thus, the manifold 11 is evacuated. Subsequently, the sample cell 12 retaining the solid sample A in the sample retaining portion 12a thereof and the reference cells 13 and 14 are respectively connected to the connection pipes 21, 22 and 23, and then all the electromagnetic valves V1 to V9 are once closed.

After air in the sample cell 12 is introduced into the manifold 11 with the electromagnetic valve V1 being open, the manifold 11 is evacuated with the electromagnetic valve V1 being closed and with the electromagnetic valve V9 being open. This operation is repeatedly performed until a gas pressure detected by the pressure sensor S1 is reduced to not higher than 10 kPa. The cell connection pipe 21 and the sample cell 12 located downstream of the electromagnetic valve V1 are thus gradually evacuated through the manifold 11, whereby the solid sample A retained in the sample cell 12 is effectively prevented from scattering around.

Subsequently, the reference cells 13, 14 are evacuated with the electromagnetic valve V1 being closed and with the electromagnetic valves V2, V3 and V9 being open. Then, the electromagnetic valve V1 is opened again, and the evacuation of the manifold 11, the sample cell 12 and the reference cells 13, 14 is continued until a gas pressure detected by the vacuum sensor S5 is reduced below 0.007 kPa.

Determination of Dead Volume of First Reference Cell

After completion of the initialization of the apparatus, the dead volume of the first reference cell is determined.

First, the helium gas is fed at 101 kPa into the manifold 11. More specifically, an internal gas pressure of the manifold 11 is measured by the pressure sensor S1, and then the electromagnetic valve V7 is opened. If a difference between the internal gas pressure of the manifold 11 and a target feed pressure (101 kPa) is not smaller than 1.5 kPa, the electromagnetic valve V5 is opened, and the helium gas is fed into the manifold 11 through the gas inlet pipe 25 having the needle valve V11 until the difference is reduced below 1.0 kPa. When the difference is reduced below 1.0 kPa, the electromagnetic valve V5 is closed and the electromagnetic valve V4 is opened. Thus, the helium gas is fed into the manifold 11 through the gas inlet pipe 24 having the needle valve V10 until the internal gas pressure of the manifold 11 reaches the target feed pressure. When the internal gas pressure of the manifold 11 reaches the target feed pressure, the electromagnetic valves V4 and V7 are closed. Thereafter (after a lapse of about five seconds), an actual internal gas pressure Pi of the manifold 11 is measured by the pressure sensor S1.

After the helium gas is introduced from the manifold 11 into the first reference cell 13 with the electromagnetic valve V2 being open, an internal gas pressure of the manifold 11 and an internal gas pressure of the reference cell 13 are respectively measured by the pressure sensors S1 and S3, and an average Pe of these internal gas pressures is calculated. A dead volume Vd(REF1, RT) of the reference cell 13 at an ambient temperature is calculated from the following expression (1) on the basis the gas pressures Pi and Pe determined through the actual measurement.

$$Vd(REF1, RT) = \left(\frac{Pi}{Pe} - 1\right) \times Vs \tag{1}$$

Thereafter, the helium gas is fed at 101 kPa into the manifold 11 and the reference cell 13 by the aforesaid gas feeding method with the electromagnetic valve V2 being open, and then the electromagnetic valve V2 is closed.

Determination of Dead Volume of Second Reference Cell

First, the nitrogen gas is fed at 101 kPa into the manifold 11 by the same gas feeding method as employed for the determination of the dead volume of the first reference cell 13, and then an actual internal gas pressure Pi of the manifold 11 is measured by the pressure sensor S1.

After the nitrogen gas is introduced from the manifold 11 into the second reference cell 14 with the electromagnetic valve V3 being open, an internal gas pressure of the manifold 11 and an internal gas pressure of the reference cell 14 are respectively measured by the pressure sensors S1 and S4, and an average Pe of these internal gas pressures are calculated. A dead volume Vd(REF2, RT) of the reference cell 14 at an ambient temperature is calculated from the following expression (2) on the basis the gas pressures Pi and Pe determined through the actual measurement.

$$Vd(REF2, RT) = \left(\frac{Pi}{Pe} - 1\right) \times Vs \quad (2)$$

Thereafter, the nitrogen gas is fed at 101 kPa into the manifold 11 and the reference cell 14 by the aforesaid gas feeding method with the electromagnetic valve V3 being open, and then the electromagnetic valve V3 is closed.

Preparation for Measurement of Adsorption Amount

After completion of the determination of the dead volumes Vd(REF1, RT), Vd(REF2, RT) of the reference cells 13, 14 at the ambient temperature, a preparatory operation is performed for the measurement of the amount of the nitrogen gas adsorbed on the solid sample A.

After an internal gas pressure Pi(REF1, RT) of the first reference cell 13 and an internal gas pressure Pi(REF2, RT) of the second reference cell 14 are simultaneously measured by the pressure sensors S3 and S4, respectively, the constant temperature bath 15 containing the liquid nitrogen is set so that the sample retaining portion 12a of the sample cell 12, the first reference cell 13 and the second reference cell 14 are immersed in the liquid nitrogen.

Subsequently, an internal gas pressure Pi(REF2,LN$_2$) of the second reference cell 14 is measured by the pressure sensor S4, and a dead volume Vd(REF2,LN$_2$) of the second reference cell 14 under this temperature condition is calculated from the following expression (3):

$$Vd(REF2, LN_2) = \frac{Pi(REF2, RT)}{Pi(REF2, LN_2)} \times Vd(REF2, RT) \quad (3)$$

Then, a nitrogen gas feed pressure required for condensation of the nitrogen gas is calculated on the basis of the internal gas pressure Pi(REF2,LN$_2$) of the second reference cell 14 and the dead volume Vd(REF2,LN$_2$) of the second reference cell 14. The nitrogen gas is fed into the second reference cell 14 via the manifold 11 at the feed pressure thus calculated thereby to be condensed within the second reference cell 14. Then, the electromagnetic valve V3 is closed.

Finally, the electromagnetic valves V8, V9 are opened, and the manifold 11 is evacuated until a gas pressure detected by the vacuum sensor S5 is reduced to not higher than 7 Pa. Then, all the electromagnetic valves V1 to V9 are closed.

Measurement of Initial Dead Volume of Sample Cell

The helium gas is fed from the non-adsorbable gas cylinder 17 into the manifold 11 by the aforesaid gas feeding method and, at this time, an internal gas pressure P1i of the manifold 11 is measured by the pressure sensor S1.

After the helium gas is introduced from the manifold 11 into the sample cell 12 with the electromagnetic valve V1 being open, the electromagnetic valve V1 is closed, and an internal gas pressure P1e of the manifold 11 and an internal gas pressure P2e of the sample cell 12 are respectively measured by the pressure sensors S1 and S2. An initial dead volume Vd$_0$(SNPL,LN$_2$) of the sample cell 12 under this temperature condition is calculated from the following expression (4):

$$Vd_0(SNPL, LN_2) = \frac{(P1i - P1e) \times Vs}{P2e} \quad (4)$$

When the internal gas pressure P2e of the sample cell 12 is measured, an initial internal gas pressure P3$_0$ of the first reference cell 13 is measured by the pressure sensor S3. Then, an initial dead volume Vd$_0$(REF1,LN$_2$) of the first reference cell 13 under this temperature condition is calculated from the following expression (5):

$$Vd_0(REF1, LN_2) = \frac{Pi(REF1, RT)}{P3_0} \times Vd(REF1, RT) \quad (5)$$

Finally, the gas is introduced from the sample cell 12 into the manifold 11 with the electromagnetic valve V1 being open, and then the manifold 11 is evacuated with the electromagnetic valve V1 being closed and with the electromagnetic valve V9 being open. This operation is repeatedly performed until a gas pressure detected by the pressure sensor S1 is reduced to not higher than 10 kPa. When the gas pressure detected by the pressure sensor S1 is reduced to not higher than 10 kPa, the manifold 11 and the gas inlet pipes 24, 25 are evacuated with the electromagnetic valves V8, V9 being open until a gas pressure detected by the vacuum sensor S5 is reduced to not higher than 7 Pa. Then, the sample cell 12 is evacuated with the electromagnetic valve V1 being open, and all the electromagnetic valves V1 to V9 are closed.

Measurement of Gas Adsorption Amount

First, a target nitrogen gas feed pressure is calculated on the basis of the internal gas pressures of the sample cell 12 and the second reference cell 14. Then, the nitrogen gas is fed into the manifold 11 by the aforesaid gas feeding method until the target feed pressure is reached, and an actual internal gas pressure P1$i_k$ of the manifold 11 is measured by the pressure sensor S1.

By opening the electromagnetic valve V1 for three seconds, the nitrogen gas is introduced from the manifold 11 into the sample cell 12 thereby to be adsorbed on the solid sample A. After the nitrogen gas reaches an adsorption equilibrium, the electromagnetic valve V1 is closed. Then, an internal gas pressure P1$e_k$ of the manifold 11, an internal gas pressure P2$e_k$ of the sample cell 12 and internal gas pressures P3$_k$ and P4$_k$ of the reference cells 13 and 14 are respectively measured by the pressure sensors S1, S2, S3 and S4. The internal gas pressure P4$_k$ of the second reference cell 14 thus measured is a saturation vapor pressure of the nitrogen gas at this time point.

A dead volume Vd$_k$(SNPL,LN$_2$) of the sample cell 12 at this time point is different from the initial dead volume Vd$_0$(SNPL,LN$_2$) of the sample cell 12 measured immediately after the sample cell is set in the constant temperature bath 15. However, the difference (i.e., a change DVd in the dead volume of the sample cell 12) is equal to a change in the dead volume of the first reference cell 13 from the initial dead volume Vd$_0$(REF1,LN$_2$) measured when the initial dead volume Vd$_0$(SNPL,LN$_2$) of the sample cell 12 is measured. Therefore, the change DVd in the dead volume of the sample cell 12 is calculated from the following expression (6):

$$DVd = \left(1 - \frac{P3_0}{P3_k}\right) \times Vd_0(REF1, LN_2) \quad (6)$$

Then, the dead volume $Vd_k(SNPL,LN_2)$ of the sample cell 12 at this time point is calculated from the following expression (7):

$$Vd_k(SNPL,LN_2) = Vd_0(SNPL,LN_2) - DVd \quad (7)$$

Then, the adsorbed nitrogen gas amount Q is calculated from the following expression (8) on the basis of the measured internal gas pressures $P1i_k$ and $P1e_k$ of the manifold 11, the measured internal gas pressure $P2e_k$ of the sample cell 12 and the calculated dead volume $Vd_k(SNPL,LN_2)$.

$$Q = \frac{(P1i_k - P1e_k) \times Vs + P2e_k \times Vd_k(SNPL, LN_2)}{RT} \quad (8)$$

wherein R is the gas constant, and T is the ambient temperature.

In the gas adsorption measuring apparatus 1, the initial dead volume $Vd_0(SNPL,LN_2)$ of the sample cell 12 and the initial dead volume $Vd_0(REF1,LN_2)$ of the first reference cell 13 are simultaneously determined and, when the gas adsorption on the solid sample A is determined, the change DVd in the dead volume of the sample cell 12 is calculated on the basis of the internal gas pressure $P3_k$ of the reference cell 13 measured at this time point, the initial dead volume $Vd_0(REF1,LN_2)$ of the reference cell 13 preliminarily measured, and the initial internal gas pressure $P3_0$ of the reference cell 13 measured at the time point of the measurement of the initial dead volume $Vd_0(REF1,LN_2)$ of the reference cell 13 to correct the initial dead volume $Vd_0(SNPL,LN_2)$ of the sample cell 12 preliminarily measured. The corrected dead volume is employed for the determination of the gas adsorption on the solid sample A. Hence, there is no need to perform the troublesome operation for determining the dead volume of the sample cell 12 every time the gas adsorption on the solid sample A is measured. In addition, there is no need to maintain the environment of the sample cell 12 in a constant state as in the conventional volumetric gas adsorption measuring method. Therefore, the gas adsorption on the solid sample A can easily and accurately be determined.

Since the surface level of the liquid nitrogen changes along the same inner diameter portions of the sample cell 12 and the reference cell 13 immersed in the liquid nitrogen within the constant temperature bath 15, the change DVd in the dead volume of the sample cell 12 is equal to the change in the dead volume of the reference cell 13 as described above. Therefore, the dead volume of the sample cell 12 can easily be corrected.

In the gas adsorption measuring apparatus 1 described above, the dead volume Vd(REF1, RT) of the reference cell 13 at the ambient temperature is preliminarily measured and, when the initial dead volume $Vd_0(SNPL,LN_2)$ of the sample cell 12 is measured with the reference cell 13 being immersed in the liquid nitrogen within the constant temperature bath 15, the internal gas pressure of the reference cell 13 is measured for the calculation of the initial dead volume $Vd_0(REF1,LN_2)$ of the reference cell 13 at this time point. However, the method for determining the initial dead volume $Vd_0(REF1,LN_2)$ of the reference cell 13 is not limited thereto. Instead of the dead volume Vd(REF1, RT) of the reference cell 13, a dead volume $Vd(REF1,LN_2)$ of the reference cell 13 may be measured with the reference cell 13 being immersed in the liquid nitrogen within the constant temperature bath 15 for the determination of the initial dead volume $Vd_0(REF1,LN_2)$ of the reference cell 13.

In the gas adsorption measuring apparatus 1 described above, the reference cell 13 has the same inner diameter as the portion of the sample cell 12 (excluding the sample retaining portion 12a) which is subjected to the change in the surface level of the liquid nitrogen in the constant temperature bath 15 when the sample cell 12 and the reference cell 13 are immersed in the liquid nitrogen. However, the construction of the reference cell 13 is not limited thereto. Alternatively, a reference cell having an inner diameter different from the inner diameter of the sample cell 12 may be employed.

Where such a reference cell is employed, however, a change in the dead volume of the reference cell is not equal to the change in the dead volume of the sample cell 12. Therefore, the change in the dead volume of the reference cell should be corrected according to the inner diameter of the sample cell 12 for the calculation of the dead volume of the sample cell 12.

Figure 2:
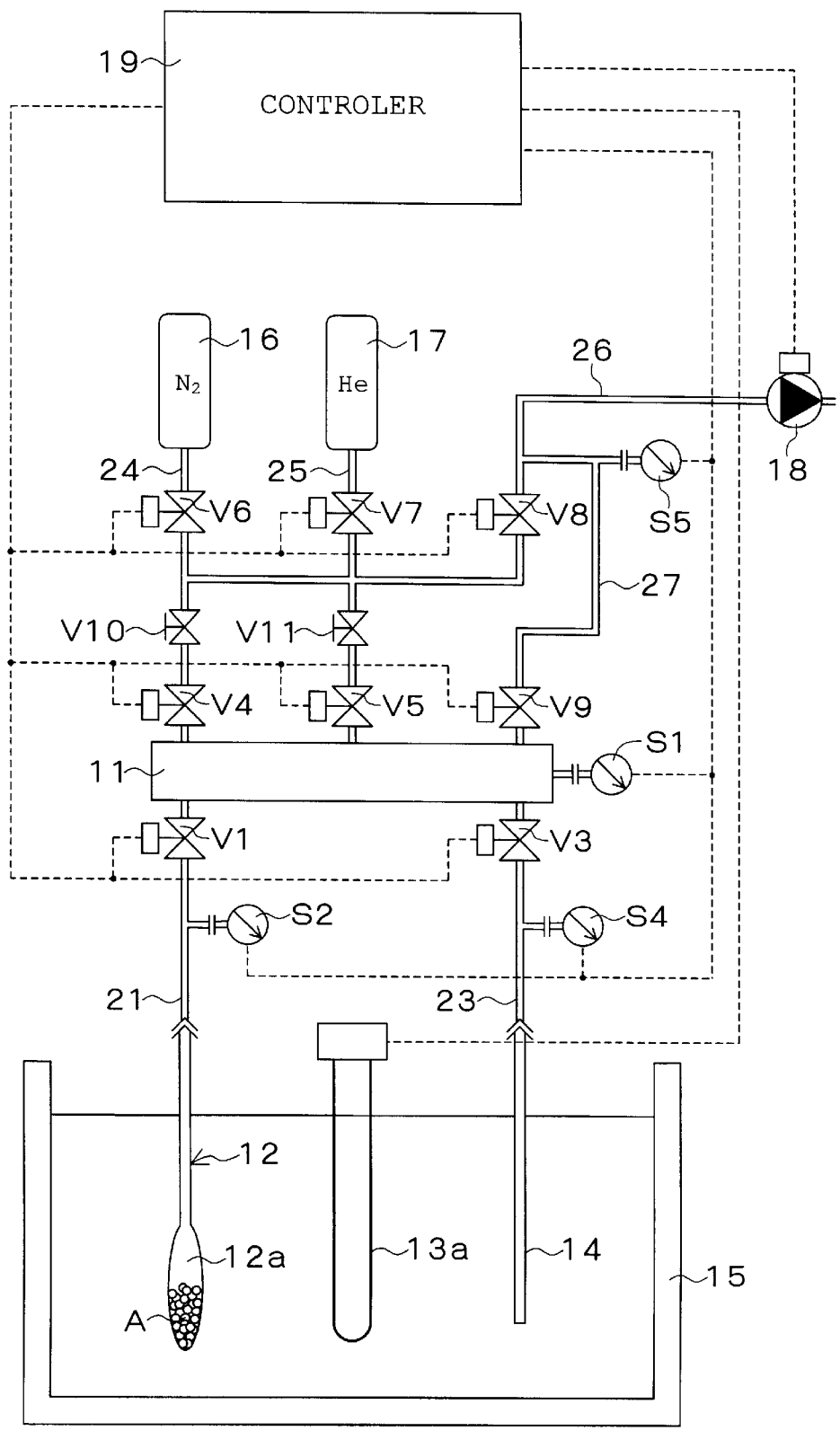
FIG. 2 is a diagram schematically illustrating the construction of a gas adsorption measuring apparatus according to another embodiment of the present invention.

In the gas adsorption measuring apparatus 1 described above, the change DVd in the dead volume of the sample cell 12 is calculated on the basis of the internal gas pressure $P3_k$ of the reference cell 13 measured when the gas adsorption on the solid sample A is measured. However, the method for determining the change DVd in the dead volume of the sample cell 12 is not limited thereto. For example, a platinum wire sensor 13a having a resistance value which is variable proportionally to the change in the surface level of the cryogenic coolant within the constant temperature bath 15 may be employed instead of the reference cell 13 in a gas adsorption measuring apparatus 2 as shown in FIG. 2. More specifically, the platinum wire sensor 13a is immersed together with the sample cell 12 in the cryogenic coolant within the constant temperature bath 15. Subsequently, an initial dead volume $Vd_0(SNPL,LN_2)$ of the sample cell 12 and an initial resistance value $R_0$ of the platinum wire sensor 13a are measured with the surface level of the cryogenic coolant being located at one level, and a dead volume $Vd_1(SNPL,LN_2)$ of the sample cell 12 and a resistance value $R_1$ of the platinum wire sensor 13a are measured with the surface level of the cryogenic coolant being located at the other level. Then, the ratio of the change in the dead volume of the sample cell 12 to a change in the resistance value of the platinum wire sensor 13a occurring due to the change in the surface level of the cryogenic coolant is preliminarily determined as a conversion factor AVd from the following expression (9):

$$AVd = \frac{Vd_0(SNPL, LN_2) - Vd_1(SNPL, LN_2)}{R_0 - R_1} \quad (9)$$

When the gas adsorption on the solid sample is to be calculated, a resistance value $R_k$ of the platinum wire sensor 13a and an internal gas pressure of the sample cell 12 are measured, and a change DVd in the dead volume of the sample cell 12 at this time point is calculated from the following expression (10) on the basis of the resistance value $R_k$ of the platinum wire sensor 13a thus measured, the initial resistance value $R_0$ of the platinum wire sensor 13a measured at the time point of the measurement of the initial dead volume of the sample cell 12, and the conversion factor AVd preliminarily determined.

$$DVd = \left(1 - \frac{R_0}{R_k}\right) \times AVd \quad (10)$$

Then, the dead volume $Vd_k$ of the sample cell 12 at this time point is calculated on the basis of the change DVd in the dead volume for the calculation of the gas adsorption on the solid sample.

In this gas adsorption measuring apparatus 2, the platinum wire sensor 13a having a resistance value which is variable proportionally to the change in the surface level of the cryogenic coolant is employed instead of the reference cell 13. However, a sensor to be employed is not limited to the platinum wire sensor. Any of various sensors may be employed as long as the physical property value thereof varies proportionally to the change in the surface level of the cryogenic coolant.

Figure 3:
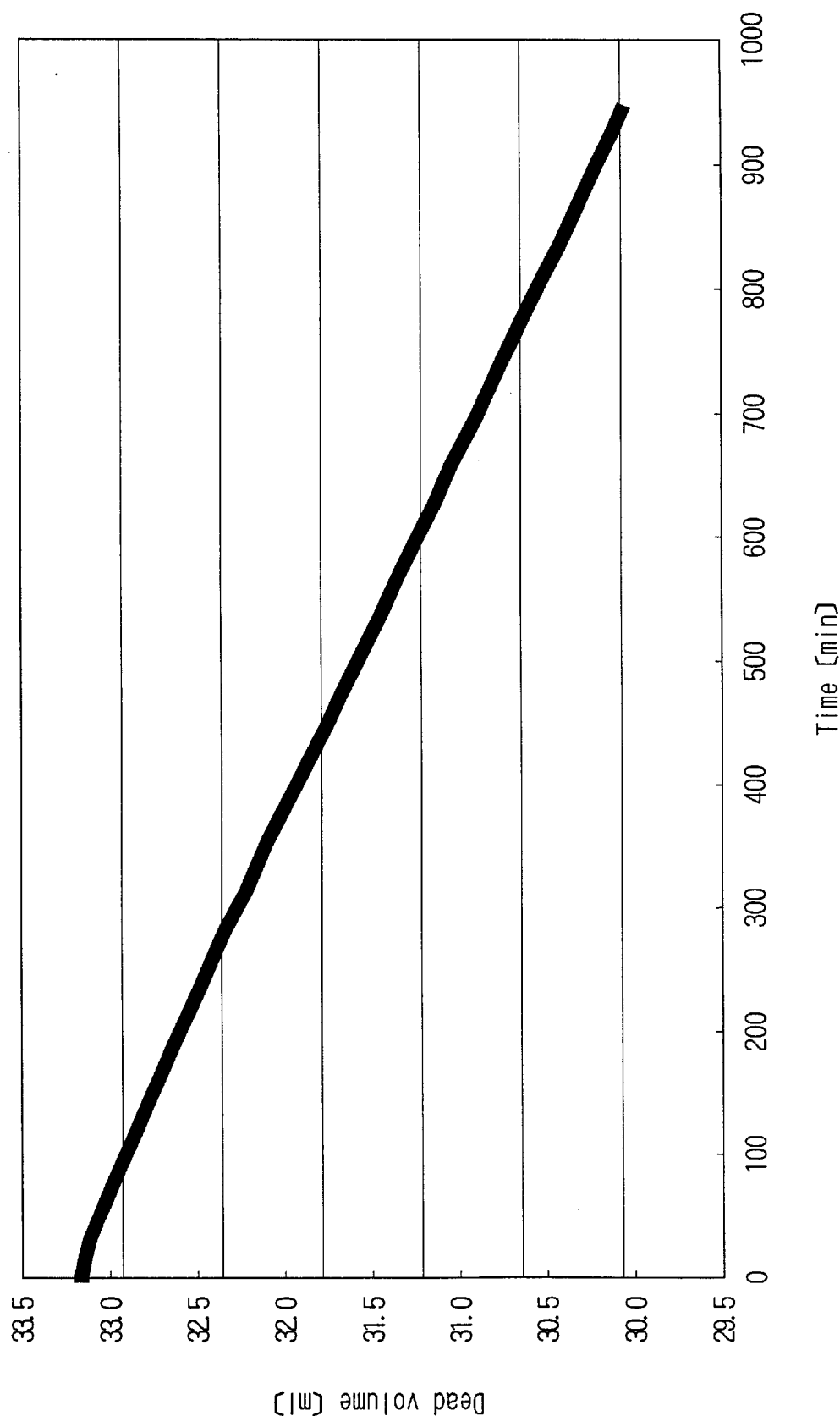
FIG. 3 is a graph illustrating a change in the dead volume of a sample cell occurring due to lowering of the surface level of a cryogenic coolant contained in a constant temperature bath.
Figure 4:
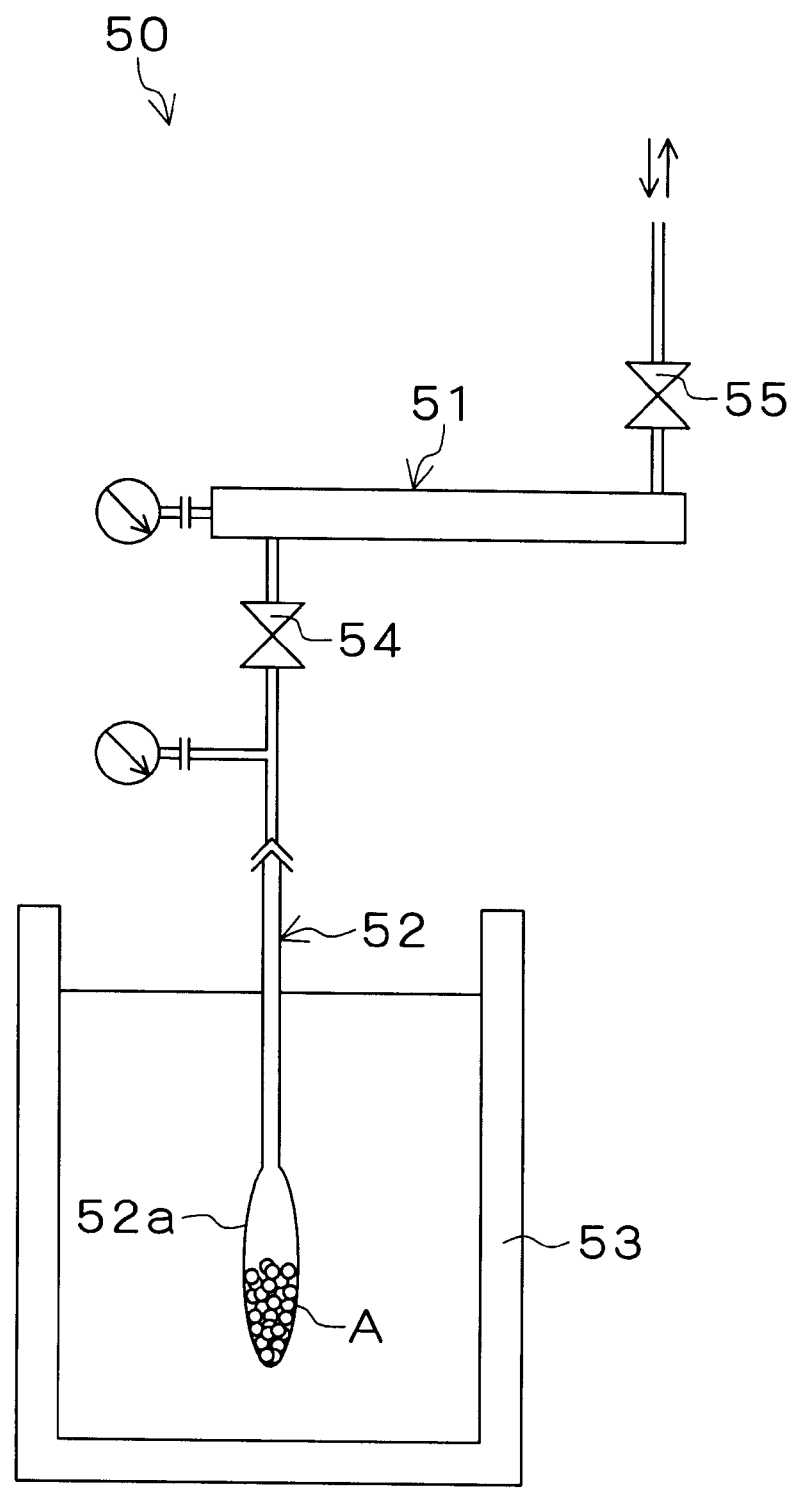
FIG. 4 is a diagram schematically illustrating the construction of a conventional gas adsorption measuring apparatus.

In the gas adsorption measuring apparatus 1 described above, the internal gas pressure $P3_k$ of the reference cell 13 is measured for the calculation of the change DVd in the dead volume of the sample cell 12 every time the gas adsorption on the solid sample A is measured. However, the method for determining the change in the dead volume of the sample cell is not limited thereto. For example, the change in the dead volume of the sample cell occurring with time due to the lowering of the surface level of the cryogenic coolant within the constant temperature bath as shown in FIG. 3 may preliminarily be determined as a function of time for each sample cell. When the gas adsorption on the solid sample A is to be measured, the change in the dead volume of the sample cell 12 is calculated from the aforesaid function on the basis of the time elapsed from the measurement of the initial dead volume of the sample cell 12 for the correction of the initial dead volume of the sample cell previously measured. Then, the amount of the gas adsorbed on the solid sample A is calculated by employing the corrected dead volume of the sample cell 12.

Where the change in the dead volume of the sample cell is to be calculated from the preliminarily determined function, there is no need to measure the dead volume of the reference cell 13 and the internal gas pressure of the reference cell 13, so that the provision of the reference cell 13 may be obviated.

In the gas adsorption measuring apparatus 1 described above, the single sample cell 12 is connected to the manifold 11 for the measurement of the gas adsorption on the single solid sample A. However, the number of sample cells is not limited to one. By connecting a plurality of sample cells to the manifold, the amounts of the gas adsorbed on plural types of solid samples can simultaneously be measured.

In the gas adsorption measuring apparatus 1 described above, the reference cell 14 for the measurement of the saturation vapor pressure is provided, and the pressure of the adsorbable gas (nitrogen gas) confined in the reference cell 14 is measured for the determination of the saturation vapor pressure of the adsorbable gas every time the gas adsorption is measured. However, the method for the determination of the saturation vapor pressure of the adsorbable gas is not limited thereto. A saturation vapor pressure value cited in a technical literature may be employed as the saturation vapor pressure. In this case, there is no need to provide the reference cell for the measurement of the saturation vapor pressure.

While the present invention has been described in detail by way of the embodiment thereof, it should be understood that the foregoing disclosure is merely illustrative of the technical principles of the present invention but not limitative of the same. The spirit and scope of the present invention are to be limited only by the appended claims.

What is claimed is:

1. A method for measuring an amount of a gas adsorbed on a solid sample, the method comprising:
    a preparatory process which comprises the steps of:
        preliminarily determining a dead volume of a reference cell for determination of a dead volume of a sample cell which retains the solid sample and, at this time point, filling and confining the gas in the reference cell;
        measuring an initial dead volume of the sample cell and an initial internal gas pressure of the reference cell with the sample cell and the reference cell being immersed in a cryogenic coolant contained in a constant temperature bath; and
        calculating an initial dead volume of the reference cell at a time point of the measurement of the initial dead volume of the sample cell on the basis of the initial internal gas pressure of the reference cell and the preliminarily measured dead volume of the reference cell; and
    a gas adsorption determining process which comprises the steps of:
        feeding the gas into a reference volume portion having a known geometric volume with the sample cell and the reference cell being immersed in the cryogenic coolant within the constant temperature bath, and measuring an internal gas pressure of the reference volume portion;
        allowing the reference volume portion to communicate with the sample cell to introduce the gas from the reference volume portion into the sample cell, and measuring an internal gas pressure of the sample cell; and
        calculating the amount of the gas adsorbed on the solid sample on the basis of the internal gas pressure of the reference volume portion, the internal gas pressure of the sample cell and the dead volume of the sample cell,
        wherein the dead volume of the sample cell to be employed for the calculation of the amount of the gas adsorbed on the solid sample is determined in the gas adsorption determining process by measuring an internal gas pressure of the reference cell at a time point of the measurement of the internal gas pressure of the sample cell, and correcting the initial dead volume of the sample cell on the basis of the internal gas pressure of the reference cell measured at the time point of the measurement of the internal gas pressure of the sample cell, the initial dead volume of the reference cell and the initial internal gas pressure of the reference cell.

2. A method as set forth in claim 1, wherein the reference cell has the same inner diameter as a portion of the sample cell which is subjected to a change in a surface level of the cryogenic coolant when being immersed in the cryogenic coolant within the constant temperature bath.

3. A method for measuring an amount of a gas adsorbed on a solid sample, the method comprising:
    a preparatory process which comprises the steps of:
        providing a sensor for determination of a dead volume of a sample cell which retains the solid sample, the sensor having a physical property value which is variable proportionally to a change in a surface level of a cryogenic coolant contained in a constant temperature bath;

measuring an initial dead volume of the sample cell and an initial physical property value of the sensor with the sample cell and the sensor being immersed in the cryogenic coolant within the constant temperature bath; and calculating, as a conversion factor, a ratio of a change in the dead volume of the sample cell to a change in the physical property value of the sensor occurring due to the change in the surface level of the cryogenic coolant; and a gas adsorption determining process which comprises the steps of:

feeding the gas into a reference volume portion having a known geometric volume with the sample cell and the sensor being immersed in the cryogenic coolant within the constant temperature bath, and measuring an internal gas pressure of the reference volume portion;

allowing the reference volume portion to communicate with the sample cell to introduce the gas from the reference volume portion into the sample cell, and measuring an internal gas pressure of the sample cell; and calculating the amount of the gas adsorbed on the solid sample on the basis of the internal gas pressure of the reference volume portion, the internal gas pressure of the sample cell, and the dead volume of the sample cell, wherein the dead volume of the sample cell to be employed for the calculation of the amount of the gas adsorbed on the solid sample is determined in the gas adsorption determining process by measuring a physical property value of the sensor at a time point of the measurement of the internal gas pressure of the sample cell, and correcting the initial dead volume of the sample cell on the basis of the physical property value of the sensor measured at the time point of the measurement of the internal gas pressure of the sample cell, the initial physical property value of the sensor, and the conversion factor.

4. A method for measuring an amount of a gas adsorbed on a solid sample, the method comprising:

a preparatory process which comprises the steps of:

immersing a sample cell retaining the solid sample in a cryogenic coolant contained in a constant temperature bath, and preliminarily determining, as a function of time, a change in a dead volume of the sample cell occurring with time due to lowering of a surface level of the cryogenic coolant within the constant temperature bath; and measuring an initial dead volume of the sample cell with the sample cell being immersed in the cryogenic coolant within the constant temperature bath; and a gas adsorption determining process which comprises the steps of:

feeding the gas into a reference volume portion having a known geometric volume with the sample cell being immersed in the cryogenic coolant within the constant temperature bath, and measuring an internal gas pressure of the reference volume portion;

allowing the reference volume portion to communicate with the sample cell to introduce the gas from the reference volume portion into the sample cell, and measuring an internal gas pressure of the sample cell; and calculating the amount of the gas adsorbed on the solid sample on the basis of the internal gas pressure of the reference volume portion, the internal gas pressure of the sample cell, and the dead volume of the sample cell, wherein the dead volume of the sample cell to be employed for the calculation of the amount of the gas adsorbed on the solid sample is determined in the gas adsorption determining process by determining an amount of the change in the dead volume of the sample cell at a time point of the measurement of the internal gas pressure of the sample cell on the basis of the function according to time elapsed from a time point of the measurement of the initial dead volume of the sample cell, and correcting the initial dead volume of the sample cell on the basis of the amount of the change in the dead volume of the sample cell at the time point of the measurement of the internal gas pressure of the sample cell.

5. A method as set forth in claim 1, wherein a plurality of sample cells respectively retaining different solid samples are immersed in the cryogenic coolant within the constant temperature bath, wherein the gas is introduced from the reference volume portion sequentially into the respective sample cells for determination of amounts of the gas adsorbed on the solid samples retained in the respective sample cells.

6. A method as set forth in claim 3, wherein a plurality of sample cells respectively retaining different solid samples are immersed in the cryogenic coolant within the constant temperature bath, wherein the gas is introduced from the reference volume portion sequentially into the respective sample cells for determination of amounts of the gas adsorbed on the solid samples retained in the respective sample cells.

7. A method as set forth in claim 4, wherein a plurality of sample cells respectively retaining different solid samples are immersed in the cryogenic coolant within the constant temperature bath, wherein the gas is introduced from the reference volume portion sequentially into the respective sample cells for determination of amounts of the gas adsorbed on the solid samples retained in the respective sample cells.

8. A method as set forth in claim 1, wherein a saturation vapor pressure of the gas is measured in the gas adsorption determining process.

9. A method as set forth in claim 3, wherein a saturation vapor pressure of the gas is measured in the gas adsorption determining process.

10. A method as set forth in claim 4, wherein a saturation vapor pressure of the gas is measured in the gas adsorption determining process.

11. An apparatus for measuring an amount of a gas adsorbed on a solid sample, the apparatus comprising:

a manifold having a known geometric volume;

a sample cell for retaining the solid sample, the sample cell being connected to the manifold via a switch valve;

a reference cell for determination of a dead volume of the sample cell, the reference cell being connected to the manifold via a switch valve;

a constant temperature bath containing a cryogenic coolant in which the sample cell and the reference cell are immersed;

a gas cylinder connected to the manifold via a switch valve;

evacuating means connected to the manifold via a switch valve;

gas pressure sensors for measuring internal gas pressures of the manifold, the sample cell and the reference cell; and control means which controls open/close operations of the respective switch valves and an evacuating operation of-the evacuating means, and performs a preparatory process and a gas adsorption determining process, the preparatory process comprising the steps of:
preliminarily determining a dead volume of the reference cell and, at this time point, filling and confining the gas in the reference cell;

measuring an initial dead volume of the sample cell and an initial internal gas pressure of the reference cell with the sample cell and the reference cell being immersed in the cryogenic coolant within the constant temperature bath; and calculating an initial dead volume of the reference cell at a time point of the measurement of the initial dead volume of the sample cell on the basis of the initial internal gas pressure of the reference cell and the preliminarily measured dead volume of the reference cell, the gas adsorption determining process comprising the steps of:

feeding the gas into the manifold with the sample cell and the reference cell being immersed in the cryogenic coolant within the constant temperature bath, and measuring an internal gas pressure of the manifold;

allowing the manifold to communicate with the sample cell to introduce the gas from the manifold into the sample cell, and measuring an internal gas pressure of the sample cell; and calculating the amount of the gas adsorbed on the solid sample on the basis of the internal gas pressure of the manifold, the internal gas pressure of the sample cell and the dead volume of the sample cell, wherein the dead volume of the sample cell to be employed for the calculation of the amount of the gas adsorbed on the solid sample is determined in the gas adsorption determining process by measuring an internal gas pressure of the reference cell at a time point of the measurement of the internal gas pressure of the sample cell, and correcting the initial dead volume of the sample cell on the basis of the internal gas pressure of the reference cell measured at the time point of the measurement of the internal gas pressure of the sample cell, the initial dead volume of the reference cell and the initial internal gas pressure of the reference cell.

12. An apparatus as set forth in claim 11, wherein the reference cell has the same inner diameter as a portion of the sample cell which is subjected to a change in a surface level of the cryogenic coolant when being immersed in the cryogenic coolant within the constant temperature bath.

13. An apparatus for measuring an amount of a gas adsorbed on a solid sample, the apparatus comprising:

a manifold having a known geometric volume;

a sample cell for retaining the solid sample, the sample cell being connected to the manifold via a switch valve;

a constant temperature bath containing a cryogenic coolant in which the sample cell is immersed;

a gas cylinder connected to the manifold via a switch valve;

evacuating means connected to the manifold via a switch valve;

gas pressure sensors for measuring internal gas pressures of the manifold and the sample cell; and control means which controls open/close operations of the respective switch valves and an evacuating operation of the evacuating means, and performs a preparatory process and a gas adsorption determining process, the preparatory process comprising the steps of:
immersing the sample cell in the cryogenic coolant within the constant temperature bath, and preliminarily determining, as a function of time, a change in a dead volume of the sample cell occurring with time due to lowering of a surface level of the cryogenic coolant within the constant temperature bath; and measuring an initial dead volume of the sample cell with the sample cell being immersed in the cryogenic coolant within the constant temperature bath, the gas adsorption determining process comprising the steps of:

feeding the gas into the manifold with the sample cell being immersed in the cryogenic coolant within the constant temperature bath, and measuring an internal gas pressure of the manifold;

allowing the manifold to communicate with the sample cell to introduce the gas from the manifold into the sample cell, and measuring an internal gas pressure of the sample cell; and calculating the amount of the gas adsorbed on the solid sample on the basis of the internal gas pressure of the manifold, the internal gas pressure of the sample cell, and the dead volume of the sample cell, wherein the dead volume of the sample cell to be employed for the calculation of the amount of the gas adsorbed on the solid sample is determined in the gas adsorption determining process by determining an amount of the change in the dead volume of the sample cell at a time point of the measurement of the internal gas pressure of the sample cell on the basis of the function according to time elapsed from a time point of the measurement of the initial dead volume of the sample cell, and correcting the initial dead volume of the sample cell on the basis of the amount of the change in the dead volume of the sample cell at the time point of the measurement of the internal gas pressure of the sample cell.

14. An apparatus as set forth in claim 11, wherein the sample cell includes a plurality of sample cells each connected to the manifold via a switch valve.

15. An apparatus as set forth in claim 13, wherein the sample cell includes a plurality of sample cells each connected to the manifold via a switch valve.

16. An apparatus as set forth in claim 11, further comprising a second reference cell connected to the manifold via a switch valve for measurement of a saturation vapor pressure of the gas to be adsorbed on the solid sample.

17. An apparatus as set forth in claim 13, further comprising a reference cell connected to the manifold via a switch valve for measurement of a saturation vapor pressure of the gas to be adsorbed on the solid sample.

* * * * *

UNITED STATES PATENT AND TRADEMARK OFFICE
CERTIFICATE OF CORRECTION

PATENT NO. : 6,595,036 B1
DATED : July 22, 2003
INVENTOR(S) : Kazuyuki Nakai

It is certified that error appears in the above-identified patent and that said Letters Patent is hereby corrected as shown below:

Column 4,
Lines 20-67, after "pressure of the" on line 20 through and before "in the dead volume of" on line 67, correct the paragraphs as follows:
-- volume of the sample cell on the basis of the internal gas pressure of the reference cell measured at the time point of the measurement of the internal gas pressure of the sample cell, the initial dead volume of the reference cell and the initial internal gas pressure of the reference cell.

The dead volume of the sample cell is herein defined as the apparent volume of the sample cell excluding the volume of the solid sample on the assumption that the sample cell is entirely maintained at the same temperature as the reference volume portion, and the dead volume of the reference cell is herein defined as the apparent volume of the reference cell on the assumption that the reference cell is entirely maintained at the same temperature as the reference volume portion.

In the gas adsorption measuring method, the dead volume of the reference cell is preliminarily measured and, at this time point, the gas is fed and confined in the reference cell. Then, the initial dead volume of the sample cell and the initial internal gas pressure of the reference cell are measured. The initial dead volume of the reference cell at the time point of the measurement of the initial dead volume of the sample cell is calculated on the basis of the initial internal gas pressure of the reference cell and the preliminarily measured dead volume of the reference cell. When the amount of the gas adsorbed on the solid sample is measured, the initial dead volume of the sample cell is corrected on the basis of the internal gas pressure of the reference cell measured at the time point of the measurement of the internal gas pressure of the sample cell, the initial dead volume of the reference cell and the initial internal gas pressure of the reference cell. Then, the corrected dead volume of the sample cell is employed for the calculation of the amount of the gas adsorbed on the solid sample. Therefore, the inventive method obviates the need for performing the troublesome operation for determining the dead volume of the sample cell every time the amount of the gas adsorbed on the solid sample is measured. In addition, there is no need to maintain the environment of the sample cell in a constant state as in the conventional volumetric gas adsorption measuring method. Hence, the amount of the gas adsorbed on the solid sample can easily and accurately be determined.

UNITED STATES PATENT AND TRADEMARK OFFICE
CERTIFICATE OF CORRECTION

PATENT NO. : 6,595,036 B1
DATED : July 22, 2003
INVENTOR(S) : Kazuyuki Nakai

It is certified that error appears in the above-identified patent and that said Letters Patent is hereby corrected as shown below:

Column 4 (cont'd),
  Where the reference cell has the same inner diameter as a portion of the sample cell which is subjected to a change in the surface level of the cryogenic coolant when being immersed in the cryogenic coolant within the constant temperature bath, a change --.

Signed and Sealed this

Twenty-seventh Day of December, 2005

JON W. DUDAS
*Director of the United States Patent and Trademark Office*